(12) United States Patent
Cimino

(10) Patent No.: US 11,583,434 B1
(45) Date of Patent: Feb. 21, 2023

(54) EXTERNALLY WEARABLE FEMALE URINARY COLLECTION AND DRAINAGE DEVICE AND RELATED COMPONENTS, SYSTEMS, KITS AND METHODS

(71) Applicant: Carolyn Cimino, Broomall, PA (US)

(72) Inventor: Carolyn Cimino, Broomall, PA (US)

( * ) Notice: Subject to any disclaimer, the term of this patent is extended or adjusted under 35 U.S.C. 154(b) by 0 days.

(21) Appl. No.: 17/804,382

(22) Filed: May 27, 2022

(51) Int. Cl.
A61F 5/455 (2006.01)
A61F 5/44 (2006.01)

(52) U.S. Cl.
CPC .......... *A61F 5/4556* (2013.01); *A61F 5/4408* (2013.01)

(58) Field of Classification Search
CPC ........ A61F 5/455; A61F 5/453; A61F 5/4408; A61F 5/44; A61F 5/449; A61F 5/451; A61F 5/4556; A61F 5/445; A61F 5/443; A61F 13/472; A61F 2013/15146; A61M 25/0017
See application file for complete search history.

(56) References Cited

U.S. PATENT DOCUMENTS

| | | |
|---|---|---|
| 3,547,123 A | 12/1970 | Sachs |
| 4,198,979 A | 4/1980 | Cooney et al. |
| 4,202,058 A | 5/1980 | Anderson |
| 4,496,355 A | 1/1985 | Hall et al. |
| 4,511,358 A | 4/1985 | Johnson, Jr. et al. |
| 4,553,968 A | 11/1985 | Komis |
| 4,692,160 A | 9/1987 | Nussbaumer |
| 4,713,065 A | 12/1987 | Koot |
| 4,713,066 A | 12/1987 | Komis |
| 4,846,817 A | 7/1989 | Mohr et al. |
| 4,886,510 A | 12/1989 | Matsuura |
| 4,889,533 A * | 12/1989 | Beecher ............... A61F 5/4407 604/355 |
| 5,032,118 A | 7/1991 | Mason |

(Continued)

FOREIGN PATENT DOCUMENTS

| | | |
|---|---|---|
| CN | 202104262 U | 1/2012 |
| CN | 202693381 U | 1/2013 |

(Continued)

OTHER PUBLICATIONS

Clark MD Enterpirses, http://clarkmdenterprises.com/clark-silicone-external-catheter/; accessed Jul. 12, 2022.

(Continued)

*Primary Examiner* — Adam Marcetich
(74) *Attorney, Agent, or Firm* — David B. Gornish; Eckert Seamans Cherin & Mellott, LLC

(57) ABSTRACT

Disclosed herein is a urinary collection and drainage device configured to be externally worn on a crotch region of a female wearer. The device includes a collection portion and a funnel portion extending from the collection portion. The collection portion is configured to substantially cover the wearer's vagina so as to receive and facilitate directional flow of urine, that the wearer excretes, into the funnel portion. The funnel portion facilitates flow of the urine to exit the device through an outlet opening of the funnel portion. Also disclosed are assemblies, kits and methods, incorporating the device in connection with additional components to enable a female wearer to urinate, in a sanitary manner, without disrobing, e.g., while standing, kneeling or in a similar position that would not obstruct the flow of urine.

22 Claims, 12 Drawing Sheets

(56) References Cited

U.S. PATENT DOCUMENTS

| | | | |
|---|---|---|---|
| 5,053,027 A | | 10/1991 | Manfredi |
| 5,057,094 A | | 10/1991 | Abbey |
| 5,607,412 A | | 3/1997 | Brown |
| 5,893,176 A | * | 4/1999 | Magiera ............... A61F 5/4556 4/144.3 |
| 5,894,608 A | * | 4/1999 | Birbara ............... A61F 5/4556 604/319 |
| 5,926,858 A | * | 7/1999 | Heller .................. A47K 11/12 4/144.1 |
| 5,935,116 A | | 8/1999 | Kristensen |
| 6,110,156 A | | 8/2000 | Mendonca |
| 6,178,559 B1 | | 1/2001 | Dennis et al. |
| 6,202,225 B1 | | 3/2001 | Beck et al. |
| 6,299,606 B1 | * | 10/2001 | Young .................. A61B 10/007 604/317 |
| 6,419,665 B1 | | 7/2002 | Cohen |
| 6,468,254 B2 | | 10/2002 | Gupton |
| 6,569,133 B2 | | 5/2003 | Cheng et al. |
| 6,599,278 B1 | | 7/2003 | Nichols |
| 6,613,027 B2 | | 9/2003 | Kulikov |
| 7,000,261 B1 | | 2/2006 | Loffredo |
| 7,018,366 B2 | | 3/2006 | Easter |
| 7,077,833 B2 | | 7/2006 | Bonham |
| 7,181,781 B1 | * | 2/2007 | Trabold ................ A61F 5/455 4/144.1 |
| 7,476,219 B2 | | 1/2009 | Ben Youssef |
| 7,658,730 B2 | | 2/2010 | Conley |
| 8,403,901 B2 | | 3/2013 | Dunlop |
| 8,486,035 B1 | | 7/2013 | Arce et al. |
| 8,597,207 B1 | * | 12/2013 | Perry .................... A61F 5/455 600/574 |
| 8,684,981 B2 | | 4/2014 | Keisic |
| 9,737,433 B2 | | 8/2017 | Joh |
| D804,654 S | | 12/2017 | Stephen |
| 10,390,989 B2 | | 8/2019 | Sanchez et al. |
| 10,588,774 B2 | | 3/2020 | Alhaqqan |
| 2004/0204695 A1 | | 10/2004 | Bisbee |
| 2004/0226073 A1 | | 11/2004 | McCullar et al. |
| 2008/0183157 A1 | | 7/2008 | Walters |
| 2008/0282441 A1 | | 11/2008 | Green |
| 2008/0300448 A1 | * | 12/2008 | Frazier ................. A61F 5/455 600/29 |
| 2009/0112171 A1 | | 4/2009 | Ng et al. |
| 2009/0131916 A1 | | 5/2009 | Chiu et al. |
| 2010/0010459 A1 | * | 1/2010 | Piette ................... A61F 5/4408 604/327 |
| 2010/0185168 A1 | * | 7/2010 | Graauw ............... A61F 5/4556 604/347 |
| 2011/0028944 A1 | | 2/2011 | Chiu et al. |
| 2011/0054426 A1 | | 3/2011 | Stewart |
| 2011/0152802 A1 | * | 6/2011 | DiCamillo ........... A61F 5/455 604/347 |
| 2011/0238023 A1 | | 9/2011 | Slayton |
| 2012/0029452 A1 | | 2/2012 | Rodsten |
| 2012/0103347 A1 | * | 5/2012 | Wheaton .............. A61F 5/453 128/885 |
| 2013/0237964 A1 | | 9/2013 | Kicos |
| 2015/0026869 A1 | | 1/2015 | Groceman |
| 2015/0135423 A1 | * | 5/2015 | Sharpe ................. A61F 5/455 4/471 |
| 2017/0239075 A1 | * | 8/2017 | Khan .................... A61F 5/455 |
| 2019/0336319 A1 | * | 11/2019 | Fallis ................... A61F 5/4408 |
| 2019/0365561 A1 | | 12/2019 | Newton et al. |
| 2020/0038230 A1 | * | 2/2020 | Leibman .............. A61F 5/4556 |
| 2020/0229964 A1 | * | 7/2020 | Staali .................... A61F 5/4408 |

FOREIGN PATENT DOCUMENTS

| | | | | |
|---|---|---|---|---|
| CN | 104336987 A | | 2/2015 | |
| CN | 104586556 A | | 5/2015 | |
| CN | 204501173 U | | 7/2015 | |
| CN | 105815843 A | | 8/2016 | |
| CN | 205729688 U | | 11/2016 | |
| CN | 106690584 A | | 5/2017 | |
| CN | 107440827 A | | 12/2017 | |
| CN | 109303634 A | | 2/2019 | |
| DE | 4212639 A1 | | 8/1992 | |
| DE | 202008000667 U1 | | 3/2008 | |
| KR | 101982939 B1 | | 5/2019 | |
| WO | WO-9636302 A1 | * | 11/1996 | ............ A61F 5/455 |
| WO | 2015/043400 A1 | | 4/2015 | |
| WO | 2019/212954 A1 | | 7/2019 | |

OTHER PUBLICATIONS

Grand Valley State University, https://www.gvsu.edu/amdi/female-urinary-collection-device-26.htm; accessed Jul. 12, 2022.
Clinisupplies Heathcare Solutions, https://www.clinisupplies.co.uk/images/resources/Prosys-Urology-brochure-v6.pdf; accessed Jul. 12, 2022.
VeganOstomy, https://www.veganostomy.ca/dressing-with-an-ostomy-clothing-for-women/; accessed Jul. 12, 2022.
AliExpress, https://www.aliexpress.com/item/4000032318676.html; accessed Jul. 12, 2022.
ProvenMed, provenmed.com/activgo-boxer; accessed Jul. 12, 2022.
Nesters, https://mynesters.com/collections/nephrostomy; accessed Jul. 12, 2022.
CathWear, https://www.cathwear.com/; accessed Jul. 12, 2022.
Campaigns & Grey, https://sites.wpp.com/wppedcream/2016/healthcare/prescription_to_consumer_traditional/on_the_go_pants/; accessed Jul. 12, 2022.
ProvenMed, https://www.provenmed.com/products; accessed Jul. 12, 2022.
Amazon, https://www.amazon.co.uk/Reusable-Collector-Silicone-Catheter-Portable/dp/B07KFC8H2H; accessed Jul. 12, 2022.
Continence Product Advisor, https://www.continenceproductadvisor.org/products/maledevices/bodywornurinals; accessed Jul. 12, 2022.
Ebay, https://www.ebay.com/itm/Incontinence-Reusable-Male-Urinal-Leg-Bag-Urinary-ExternalCatheter-1000ml-/25404811151; accessed Jul. 12, 2022.
AliExpress, https://www.aliexpress.com/item/32609029855.html; accessed Jul. 12, 2022.
PicClick, https://picclick.co.uk/Male-External-Catheter-1000ml-Drainage-Urine-Urinal-Leg-152884442778.html accessed Jul. 12, 2022.
Greenbelly, https://www.greenbelly.co/pages/best-female-urination-devices; accessed Jul. 12, 2022.
Spectrum Health, HealthBeat, https://healthbeat.spectrumhealth.org/rethinking-the-female-catheter/; accessed Jul. 12, 2022.
ShopCatheters, https://www.shopcatheters.com/p-med-assist-advantage-male-comfort-urinal-system.html; accessed Jul. 12, 2022.
Gap Year Travel Store, https://www.gapyeartravelstore.com/easy-pee-female-urination-device.html; accessed Jul. 12, 2022.
DHGate, https://www.dhgate.com/product/sex-toys-adult-supplies-urinary-incontinence/193844400.html#/seo=WAP; accessed Jul. 12, 2022.
Buck and Buck, https://www.buckandbuck.com/adaptive-clothing-guide/clothing-for-those-with-urinary-catheters.html accessed Jul. 12, 2022.
LL Medico, https://www.llmedico.com/netti-one-leg-pant-urine-bag-holder/; accessed Jul. 12, 2022.
AliExpress, https://www.aliexpress.com/i/32988456220.html; accessed Jul. 12, 2022.

\* cited by examiner

EXTERNALLY WEARABLE FEMALE URINARY COLLECTION AND DRAINAGE DEVICE AND RELATED COMPONENTS, SYSTEMS, KITS AND METHODS

BACKGROUND OF THE INVENTION

Field of the Invention

The disclosed concept relates to an externally wearable female urinary collection and drainage device, which preferably enables use without disrobing while standing (or otherwise vertically oriented with the wearer's thighs approximately axially aligned with her torso, e.g., kneeling). The disclosed concept also relates to complementary components, kits, systems and methods for using the same.

Description of Related Art

Overactive Bladder or OAB is a specific type of incontinence that affects an estimated 17% of American women over the age of 18. The most common symptom of OAB is a sudden, uncontrolled need or urge to urinate, which may occur frequently and can sometimes cause a person suffering with OAB to leak urine when this urge presents itself. This can make it difficult for an OAB sufferer to get through the day without many trips to the bathroom.

OAB is especially frustrating for an otherwise active, healthy person who wishes to engage in outdoor activities such as jogging, skiing, hiking and the like, but who is inhibited due to frequent pressing urges to urinate. The lack of bathroom access or in some cases, availability only of unsanitary public restrooms, make things very difficult for the active OAB outdoors enthusiast.

There are wearable absorbent materials on the market for OAB sufferers, such as disposable adult diapers or absorbent pads. However, such items have significant drawbacks. Once saturated, these disposable products are bulky and uncomfortable to wear. They also can leak. A person engaging in outdoor activities cannot readily disrobe to replace a saturated absorbent product with a dry one. They can also commonly cause skin irritation and become very expensive for an OAB sufferer who relies on them.

As an alternative to disposable absorbent products, there are female urinary devices on the market that help women relieve themselves like a man would at a urinal, such as the device described in U.S. Pat. No. 6,202,225. These silicone funnels are to be placed over a woman's urethra so that they can direct the expelled urine forward, like a penis would for a man, into a urinal. These products are often marketed for camping use, as women can carry the devices in their pockets and relieve themselves in the woods, if need be, without having to squat down. But this solution still requires some degree of disrobing and a private place for the woman to relieve herself.

The female urinary device in U.S. Pat. Pub. No. 2011/0054426 is described as portable. However, its configuration is not conducive to being worn under clothing comfortably, as the device has no rise in the front or back to conform to the female form. Also, the dimensions of the device would make it difficult to conceal under clothes, such as pants. Similar drawbacks exist with the urinary device described in U.S. Design Pat. No. D804,654. The device in that reference does include a rise, but the drain is located so far forward that it would protrude from the mons pubis area and could not be readily concealed when worn with clothes. The urinary device described in U.S. Pat. Pub. No. 2013/0237964 is purportedly wearable under a woman's clothing. However, the lack of length behind the drain and outlet could cause the device to overflow because the force of gravity will send urine toward the back of the funnel.

Therefore, Applicant has determined that there is a vital need for an external female urinary device that can be worn comfortably, is substantially concealable under a woman's clothing and preferably enables the wearer to urinate under her clothes while standing, without disrobing. The device should be reusable after cleaning and should be configured to avoid leakage and overflow.

SUMMARY OF THE INVENTION

Accordingly, in one aspect, the disclosed concept is a urinary collection and drainage device configured to be externally worn on a crotch region of a female wearer. The device is optionally held in place with underpants that have an opening in the crotch, so as to preferably enable the user to urinate under her clothes, without disrobing. The device includes a housing having an upper ridge configured to contact the wearer's crotch and surround her vagina. The upper ridge has a concave or crescent shape from a side view, the upper ridge surrounding an upper opening of the device. A housing wall extends from the upper ridge, the housing wall defining a collection portion and a funnel portion extending from the collection portion. The collection portion is configured to substantially cover the vagina so as to receive and facilitate directional flow of urine that the wearer excretes into the funnel portion. The funnel portion is defined by an inwardly tapered section of the housing wall and a tubular outlet to which the inwardly tapered section leads. The outlet has an outlet opening. The collection portion has a front section, a portion of which is configured to contact the wearer's mons pubis, a rear section, a portion of which is configured to contact the wearer's perineal region and opposing side sections linking the front section and back section. The side sections are concave in shape from a top view. The rear section of the ridge or device (from a top view) is preferably wider than the front section of the ridge or device. The outlet defines a central axis that is oriented at an angle inclined downwardly and towards the rear of the device. The device defines an imaginary vertically oriented central plane that intersects the front section and the rear section. The upper ridge and at least part of the collection portion is symmetrical about the central plane.

Optionally, in any embodiment of the device, the outlet is asymmetrical with respect to the central plane.

Optionally, in any embodiment of the device, the central axis of the outlet is offset by a distance greater than zero inches from the central plane.

Optionally, in any embodiment of the device, the angle is from about 14° to 17° relative to a vertical axis (Z) of a hypothetical three-dimensional Cartesian coordinate system.

Optionally, in any embodiment of the device, the upper ridge includes an outwardly projecting flange. Optionally, the flange on the front section is configured to contact the wearer's mons pubis and the flange on the rear section is configured to contact the wearer's perineal region. Optionally, from a top view, the flange is widest at the front and back sections of the ridge and tapers inward toward the middle section of the ridge.

Optionally, in any embodiment of the device, the collection portion, from a side view, is substantially crescent in shape. Some of the optional measurements of this crescent shape are described below.

Optionally, in any embodiment of the device, the depth of the collection portion is 1.25 to 2.5 inches, preferably about 1.75 inches. Optionally, in any embodiment of the device, the length of the collection portion (i.e., the opening of the collection portion, not including the flange) is 7.5 to 8.0 inches, preferably about 7.75 inches. Optionally, in any embodiment of the device, the width of the collection portion (i.e., the opening of the collection portion, not including the flange) is 2.0 to 2.5 inches, preferably about 2.25 inches.

Optionally, in any embodiment of the device, the funnel portion has an outer width that is narrower than an outer width of the collection portion.

Optionally, in any embodiment of the device, from a side view, front view and rear view, the inwardly tapered section of the housing wall defining the funnel portion has a steeper slope than the portion of the housing wall defining the collection portion, to facilitate the urine flow. The distinct geometry of the funnel portion allows it to rest beside the female's inner thigh in a manner that can be hidden under clothes, but also be easily accessed for use. Also, the funnel portion's size allows it to serve as a second collection area. The front of the inwardly tapered section of the housing wall defining the funnel portion is optionally 2 to 2.75 inches in length from the bottom of the collection portion to the top of the tubular outlet, optionally about 2.25 inches. The rear of the inwardly tapered section of the housing wall defining the funnel portion is optionally 1 to 1.75 inches in length from the bottom of the collection portion to the top of the tubular outlet, optionally about 1.375 inches. The tubular outlet is optionally 0.5 to 1 inch in length, optionally about 0.75 inches.

Optionally, in any embodiment of the device, the device includes one or more vent holes positioned on the front section, adjacent the upper ridge.

Optionally, in any embodiment of the device, the device is made from medical grade silicone having a durometer of from 60 to 80. Optionally, the device has a nominal wall thickness of 0.07 inches to 0.11 inches. Optionally, the housing wall adjacent the outlet opening has a wall thickness greater than that of the remainder of the housing wall.

Optionally, in any embodiment of the device, the device is made of a flexible material and is configured to retain its shape when worn under clothes.

Optionally, in any embodiment of the device, the inner diameter of the outlet opening is 0.25 to 0.50 inches, optionally 0.30 to 0.40 inches, optionally about 0.328 inches in order to accommodate the size and geometry of commercially available reverse barb connectors for flexible tubes and compatible urine bags.

Optionally, in any embodiment of the device, the device has a total length of 8 to 9 inches, optionally 8.5 to 9 inches, optionally about 8.75 inches and a total height of about 6 to 7 inches.

Optionally, in any embodiment of the device, the total length of the device is greater than the total height of the device.

In an optional aspect, the disclosed concept is directed to a kit. The kit includes at least one member of each of: the device according to any embodiment disclosed herein, one pair of underpants having an opening in a bottom portion thereof (in addition to leg holes that are in the bottom portion), though which the outlet of the device may protrude, a flexible tube, a connector and a urine collection container. To create a connection to the urine collection container, one end of the flexible tube is configured to be secured to the outlet opening of the device via the connector so as to establish a liquid tight fluid connection between the device and the flexible tube. The other end of the flexible tube is configured to be secured, in a liquid tight fluid connection, to a mouth of the urine collection container so as to enable liquid to flow through the flexible tube and into the urine collection container. Optionally, in any embodiment of the kit, the kit includes a pocket and/or straps for retaining the urine collection container to a leg of the wearer.

In an optional aspect, the disclosed concept is directed to a method for a female wearer to sanitarily urinate into a urine collection container that will be connected to the device, without having to undress, when she is upright and her legs and torso are oriented generally vertically e.g., standing, kneeling, or suspended above ground such as when rock climbing, and without use of an internal catheter or padding to absorb excreted urine. The method includes the following steps: (a) placing the device, according to any embodiment disclosed herein, on the crotch region of the wearer such that the upper ridge contacts the wearer's crotch and surrounds her vagina, the front section contacts the wearer's mons pubis and the rear section contacts the wearer's perineal region; (b) wearing a pair of underpants over the device, the underpants having a bottom portion that cradles the device so as to retain the device on the wearer's crotch region, the underpants having an opening in the bottom portion in addition to leg holes, the outlet of the device protruding through the opening in the bottom portion of the underpants; (c) securing a first fluid connection between the outlet opening and a first end of a flexible tube; (d) securing a second fluid connection between a second end of the flexible tube and a mouth of a urine collection container; (e) securing the urine collection container to an appendage of the wearer or onto clothing of the wearer; and (f) urinating into the device such that excreted urine flows from the device, through the flexible tube and into the urine collection container.

Optionally, in any embodiment of the method, the device may be directed into a toilet, an outhouse, the ground, etc., or to a collection container that is held adjacent to the outlet opening, as needed, by the user who prefers to carry, rather than create a connection to, or wear, a urine collection container.

Optionally, in any embodiment of the method, the device is positioned on the wearer such that the central axis of the outlet is oriented substantially perpendicular to a surface on which the wearer stands.

Optionally, in any embodiment of the method, the upper ridge includes an outwardly projecting flange. The flange on the front section contacts the wearer's mons pubis and the flange on the rear section contacts the wearer's perineal region. From a top view, the flange is widest at the front and back sections of the ridge and tapers inward toward the middle section of the ridge. Preferably the width of the ridge in the rear section is greater than the width of the ridge in the front section (from a top view), but both the front and rear sections are wider than the middle section. The device optionally includes one or more vent holes positioned on the front section, adjacent the upper ridge. Optionally, air supplied into the device from movement of the wearer's legs, escapes through the one or more vent holes to prevent the air from pressurizing the device, the flexible tube and/or the urine collection container.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
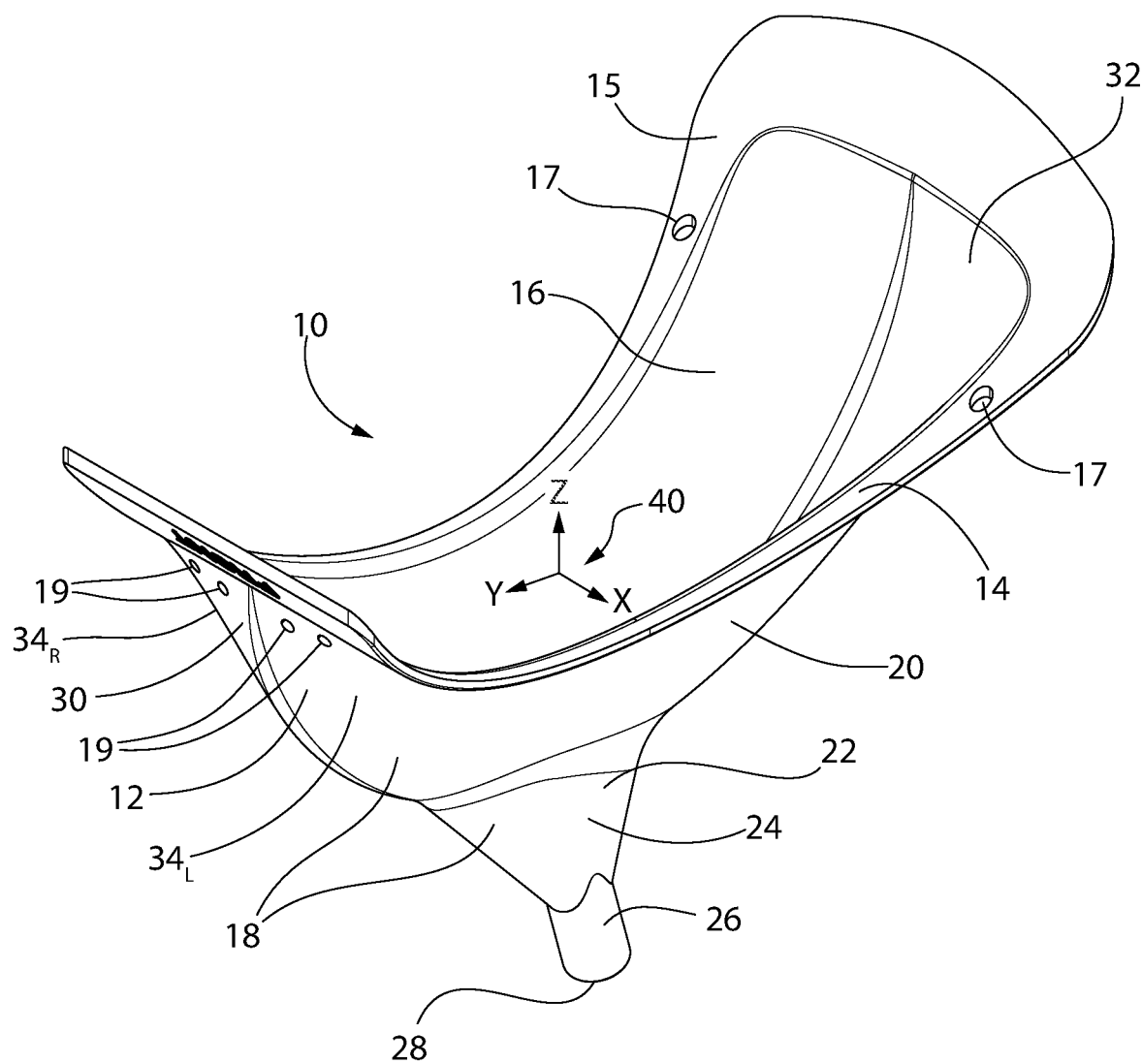
FIG. 1 is a front side isometric view of a urinary collection and drainage device according to an optional embodiment of the disclosed concept, which may be externally worn on a crotch region of a female wearer.
Figure 2:
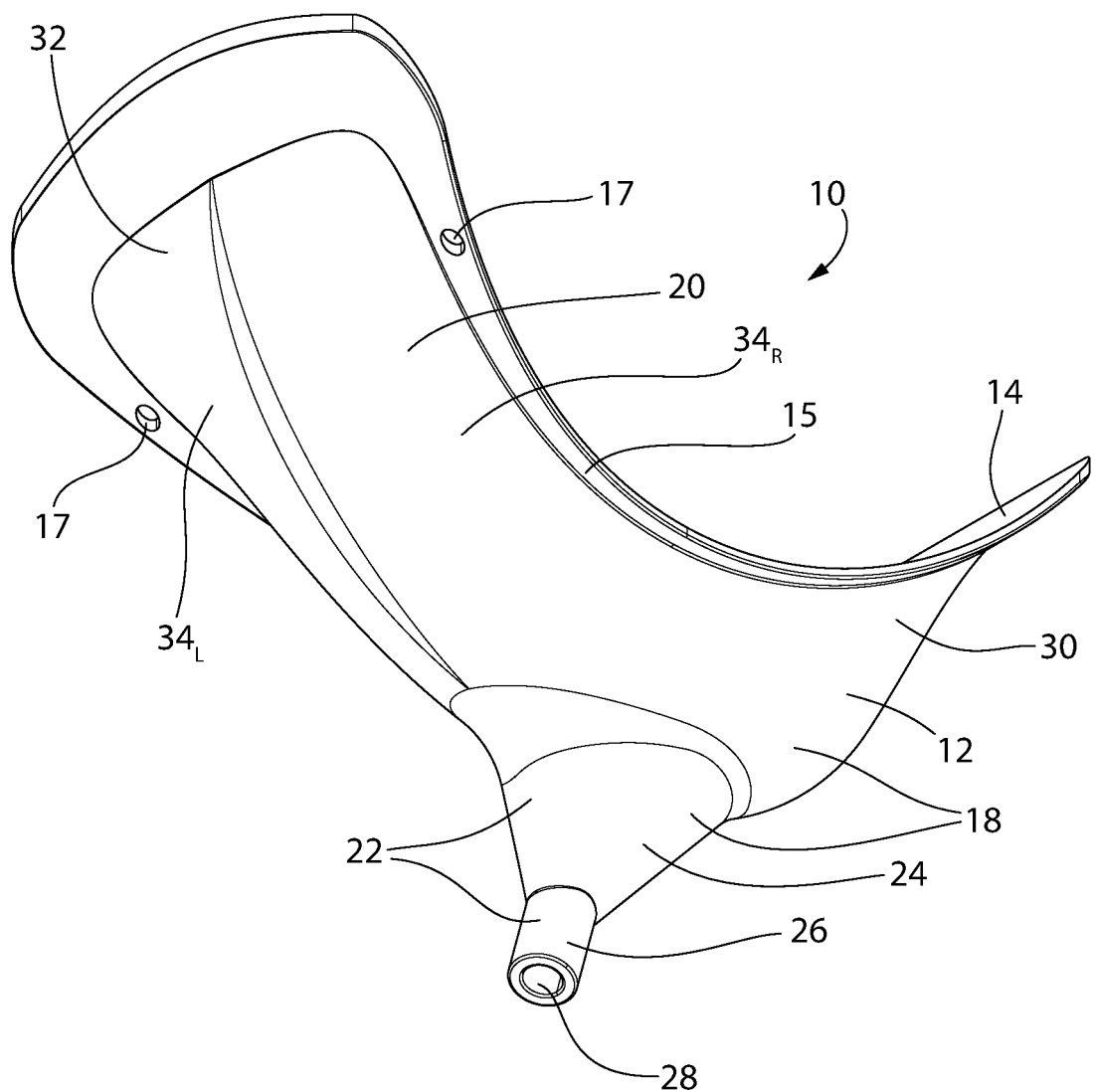
FIG. 2 is a rear side isometric view of the device of FIG. 1.

As used herein, the term "vertical" is defined as being in the direction of, oriented along or parallel to the z-axis in a three-dimensional Cartesian coordinate system. Some of the drawing figures include the x-, y- and z-axes to clarify the spatial relationship and orientation of elements of the device described herein and provide context for use of the term "vertical" or other directional/spatial relationships.

The term "front," as used herein, refers to positioning of an object on, or view looking towards, the anterior of a person. The term "rear," as used herein, refers to positioning of an object on, or view looking towards, the posterior of a person. The term "side," as used herein, refers to a view looking towards a person or object from the anatomical sagittal plane or from a plane parallel with the sagittal plane. The terms "front," "rear" and "side" are likewise used herein to refer to a portion or view of a wearable device when worn by a person in the manner intended. For example, the front of a wearable device that a person wears is positioned on the anterior of the person and the rear of the device is positioned on the posterior of the person.

The term "sagittal plane" refers to an anatomical plane, which divides the body into right and left parts.

Referring now in detail to the various figures of the drawings wherein like reference numerals refer to like parts, there are shown in FIGS. 1 to 9 various views of a urinary collection and drainage device 10 configured to be externally worn on a crotch region of a female wearer. The device 10 is configured to be worn externally and does not include an internal catheter or other element configured for insertion into the urethra. The device 10 includes a housing 12 having an upper ridge 14 configured to contact the wearer's crotch and surround her vagina. The upper ridge 14 surrounds an upper opening 16 from which extends a housing wall 18 that defines a collection portion 20 and a funnel portion 22 that extends from the collection portion 20. The collection portion 20 is configured to substantially cover the vagina so as to receive and facilitate directional flow of urine that the wearer excretes, into the funnel portion 22. The funnel portion 22 is defined by an inwardly tapered section 24 of the housing wall 18 and a tubular outlet 26 to which the inwardly tapered section 24 leads. The outlet 26 comprises an outlet opening 28 from which the urine may exit the device 10 when the device 10 is properly worn.

The collection portion 20 has a front section 30 configured to rest on the wearer's mons pubis, a rear section 32 configured to rest on the wearer's perineal region and opposing side sections $34_{L,R}$ configured to rest on the wearer's crotch region adjacent to or in contact with the wearer's respective thighs. Preferably, from a side view (e.g., FIGS. 5 and 6), the collection portion 20 has a concave or crescent shape that peaks at the front section 30 and rear section 32 and which dips down in the middle. This shape and the volume of the collection portion 20 is configured to create some distance between the wearer's crotch and the funnel portion 22 and also to work with gravity to ensure that excreted urine is directed toward the funnel portion 22 and drains out from the outlet 26. In this way, excreted urine should not significantly pool within the collection portion 20 such that the wearer's crotch should not be sitting in excreted urine when the device 10 is worn and functioning as intended.

Figure 3:
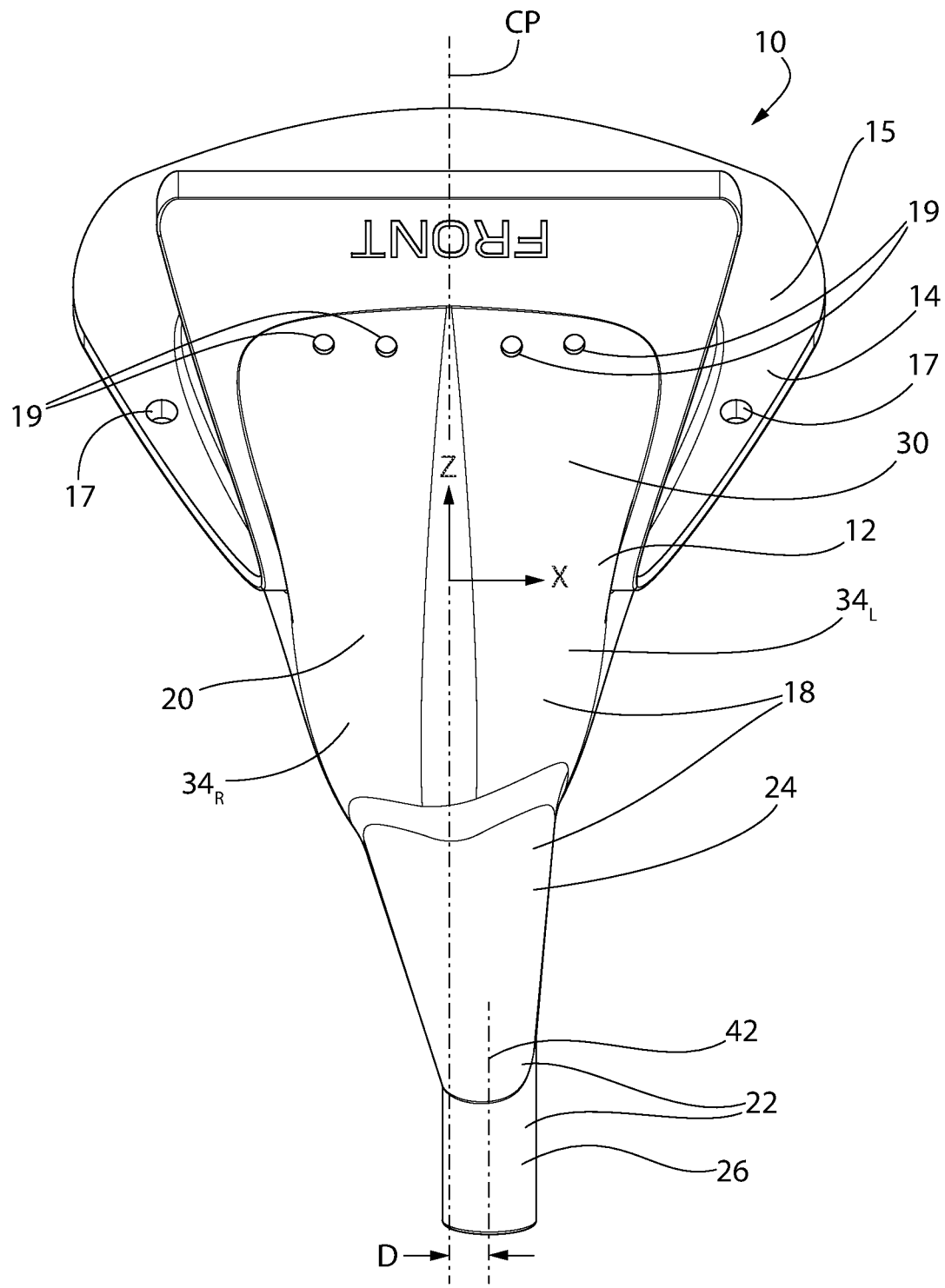
FIG. 3 is a front elevation view of the device of FIG. 1.
Figure 4:
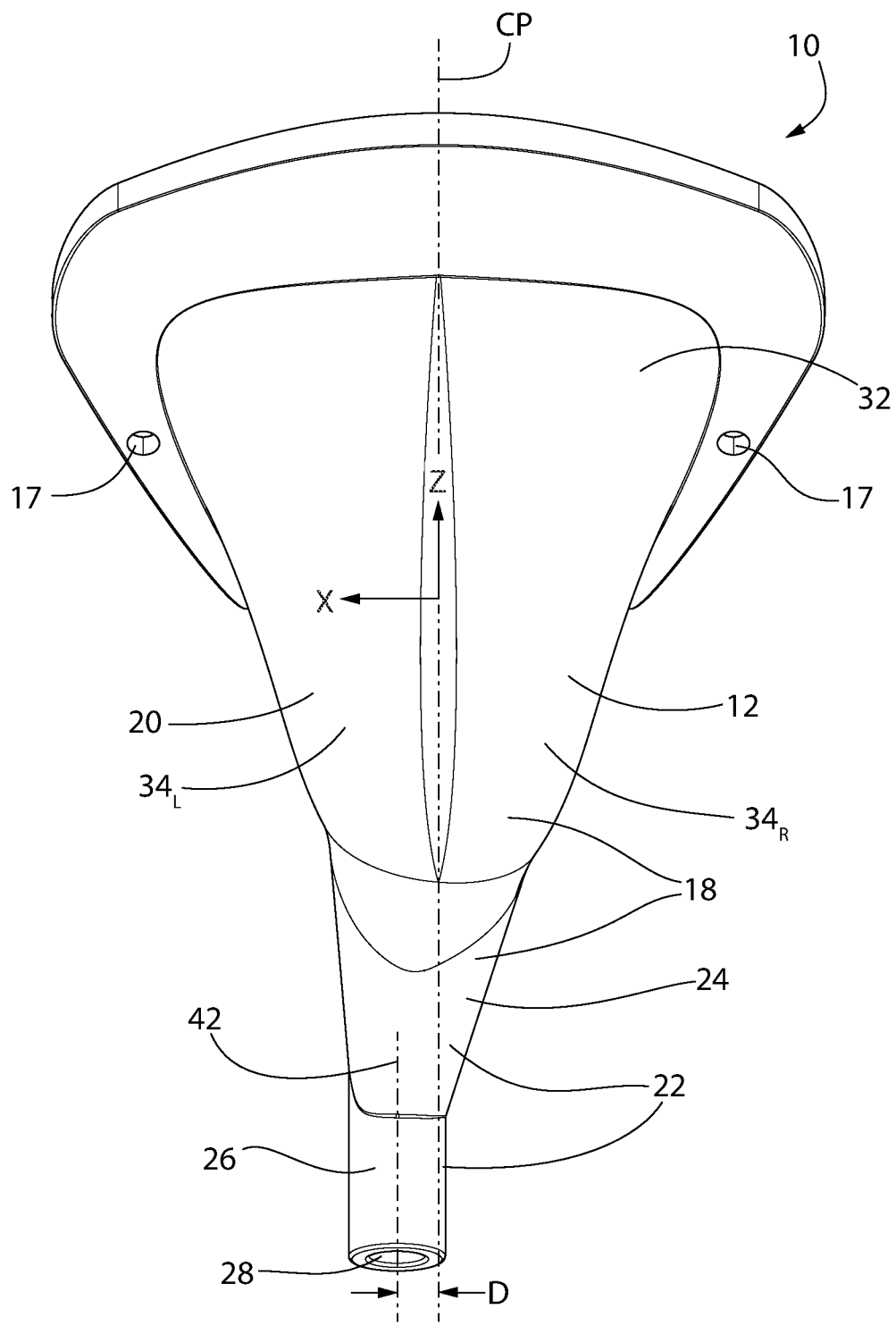
FIG. 4 is a rear elevation view of the device of FIG. 1.

The inwardly tapered section 24 of the housing wall 18 defining the funnel portion 22 preferably has a steeper slope than the portion of the housing wall 18 defining the collection portion 20, when the device 10 is viewed from side views (e.g., FIGS. 5 and 6) and front or rear views (e.g., FIG. 3 or 4, respectively). Thus, the collection portion 20 has a distinct three-dimensional geometry from that of the funnel portion 22. The funnel portion 22 functions as a large drain to help collect some of the excreted urine and move it toward the outlet opening 28. The tapered funnel portion 22 continues the downward slope from the front of collection portion 20 where the urethra expels urine and steepens the downward slope from the back of the collection portion 20, to help direct urine to the outlet opening 28. The opening wherein the collection portion 20 transitions to the funnel portion 22 is optionally about one third as long as the collection portion and optionally about half as wide. Optionally, that opening (visible in the view of FIG. 7) is 1.5 inches to 2.5 inches (preferably about 2.25 inches) long and 0.5 to 1.5 inches (preferably about 1 inch) wide. That transition section is optionally located to the front of the center of the bottom of the collection portion 20. The width of the funnel portion 22 being less than that of the collection portion 20 helps to prevent interference between the funnel portion 22 and the wearer's thighs.

From a top view (e.g., FIG. 7), the outline of the upper ridge 14 and upper opening 16 has a shape that generally follows the outline of a crotch portion of women's underpants. Namely, the upper ridge 14 and upper opening 16 are widest at the front section 30 and rear section 32 (although the rear section 32 is optionally slightly wider than the front section 30 from the top view). The upper ridge 14 and upper opening 16 follow a concave curve to a narrower middle section of the device 10 (as seen from the top view). Optionally, from a top view (e.g., FIG. 7), the front of the device 10 has a wide front (e.g., 3.5 to 4.5 inches, preferably about 4 inches) that tapers inward toward a narrower middle (e.g., 2 to 3 inches, preferably about 2.75 inches) and then tapers back out laterally to the widest section in the rear of the device 10 (e.g., 4 to 6 inches, preferably 4.5 to 5.5 inches, more preferably about 5.0 inches).

The upper ridge 14 preferably includes an outwardly projecting flange 15 around part of or the entirety of the upper ridge 14. The flange 15 is preferably widest on the front and rear sections of the upper ridge 14 and narrows in the middle. The flange 15 narrows or optionally completely disappears in the middle of the device 10. Optionally, the flange 15 on the sides is not greater than 0.5 inches in width, but may be about 0.5 inches to 1 inch wide on the front and rear sections of the upper ridge. The narrowed flange 15 or lack thereof in the middle of the upper ridge 14 may prevent interference with the wearer's legs so as to allow her to walk or run while wearing the device 10 with ease and comfort. The flange 15 optionally operates to provide one or more of the following benefits. It provides comfort to the wearer in the manner in which it follows the contours of the wearer's crotch. It increases the surface area of the upper ridge 14 to reduce pressure on the crotch and thus increase comfort. It effectively creates a seal around the wearer's crotch so as to help entrap urine that is excreted and momentarily contained within the collection portion 20. Also, it provides added surface area to integrate one or more holes or slits 17 for retaining the device 10 to underpants when worn (as discussed below).

The collection portion 20 optionally has at least one, preferably two or more small vent holes 19. The vent holes 19 are preferably positioned on the front section 30 of the device 10, preferably adjacent the upper ridge 14. The vent holes 19 may be, e.g., from 1/16 to 3/16 of an inch in diameter, although they are not limited to being circular in shape. The vent holes 19 prevent the device 10 from filling with air from activity (e.g., walking or running) of the user, particularly when the outlet 26 is connected to flexible tubing, which is in fluid communication with a urine bag or the like. Without the one or more vent holes 19, the device 10, flexible tubing and/or urine bag could fill up with air (i.e., become pressurized), like a slowly inflating balloon, when the user walks. The optional flexible tubing and urine bag (a type of urine collection container) are discussed in more detail below.

As noted above, for clarity regarding spatial relationships, direction and positional orientation of elements of the device 10, some of the drawing figures present the device 10 in the context of a hypothetical three-dimensional Cartesian coordinate system 40. The Cartesian coordinate system 40 includes three intersecting mutually perpendicular vectors, namely the x-axis (X), y-axis (Y) and z-axis (Z). As described herein and as is conventional in the fields of mathematics and three-dimensional drafting, the z-axis (Z) represents the vertical direction. The three coordinate axes (X, Y and Z) determine three coordinate planes: (1) the xy-plane (XY), which contains X and Y; (2) the yz-plane (YZ), which contains Y and Z and the xz-plane (XZ), which contains X and Z.

Figure 6:
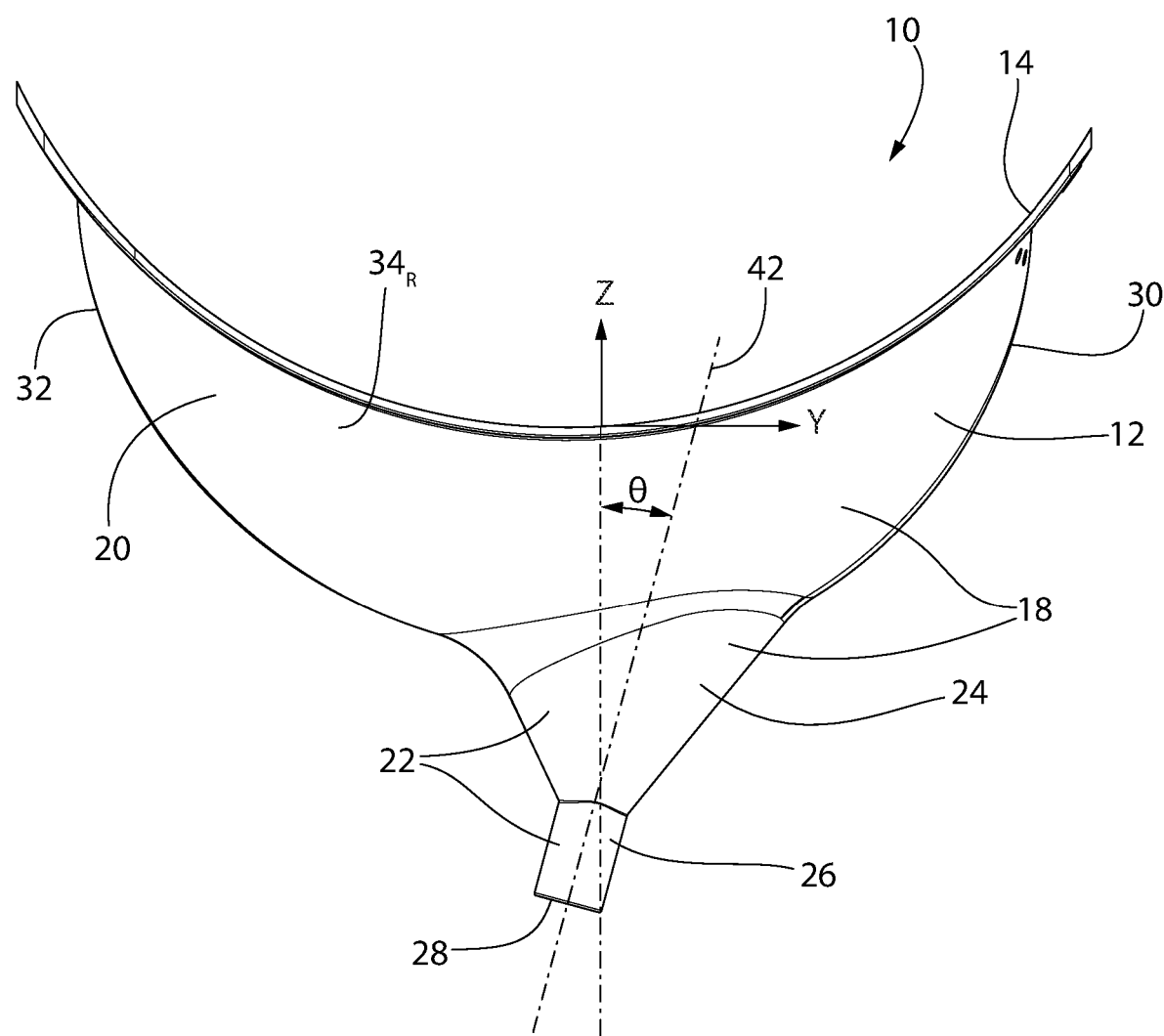
FIG. 6 is a right side elevation view of the device of FIG. 1
Figure 7:
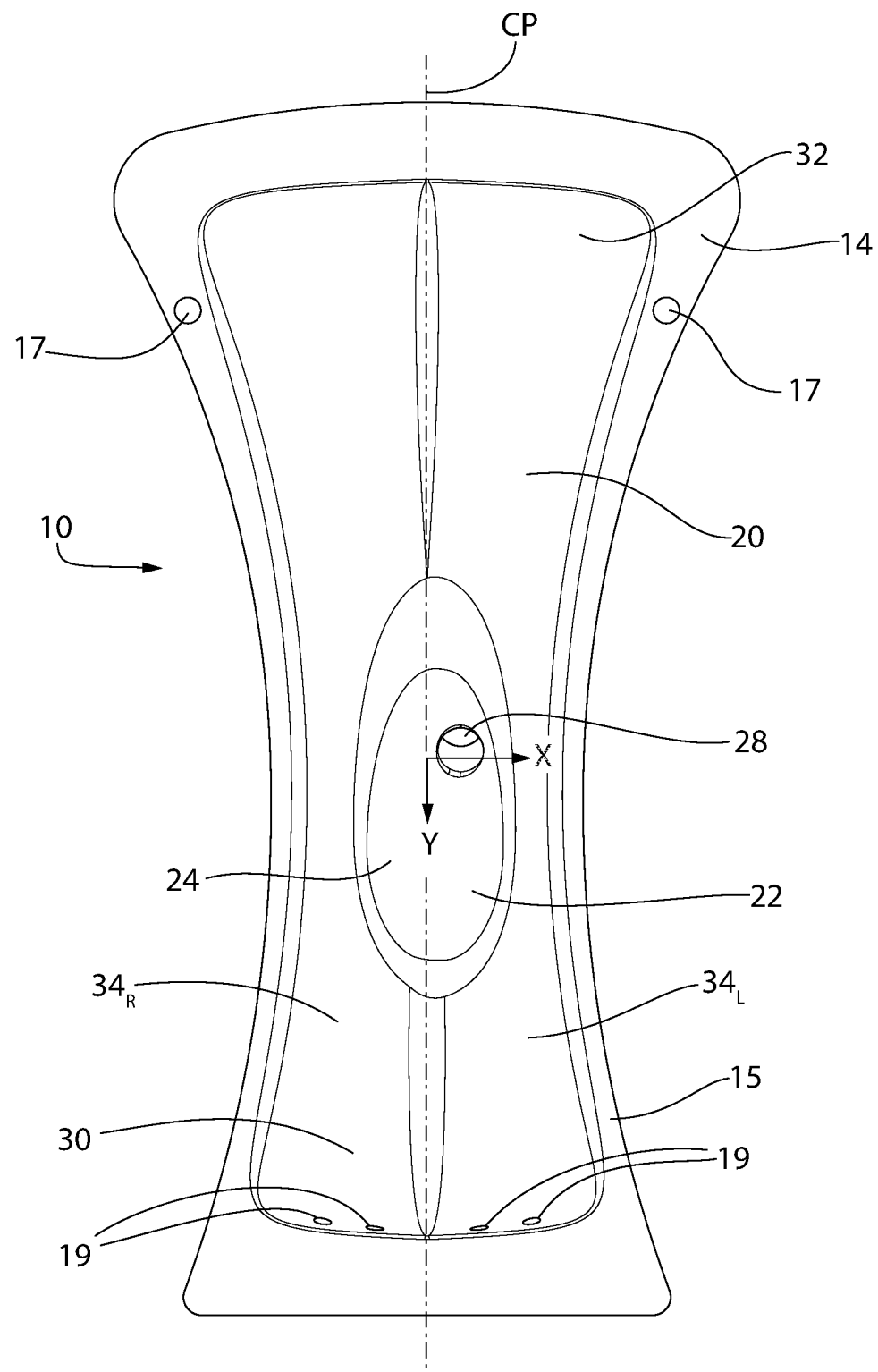
FIG. 7 is a top plan view of the device of FIG. 1.
Figure 8:
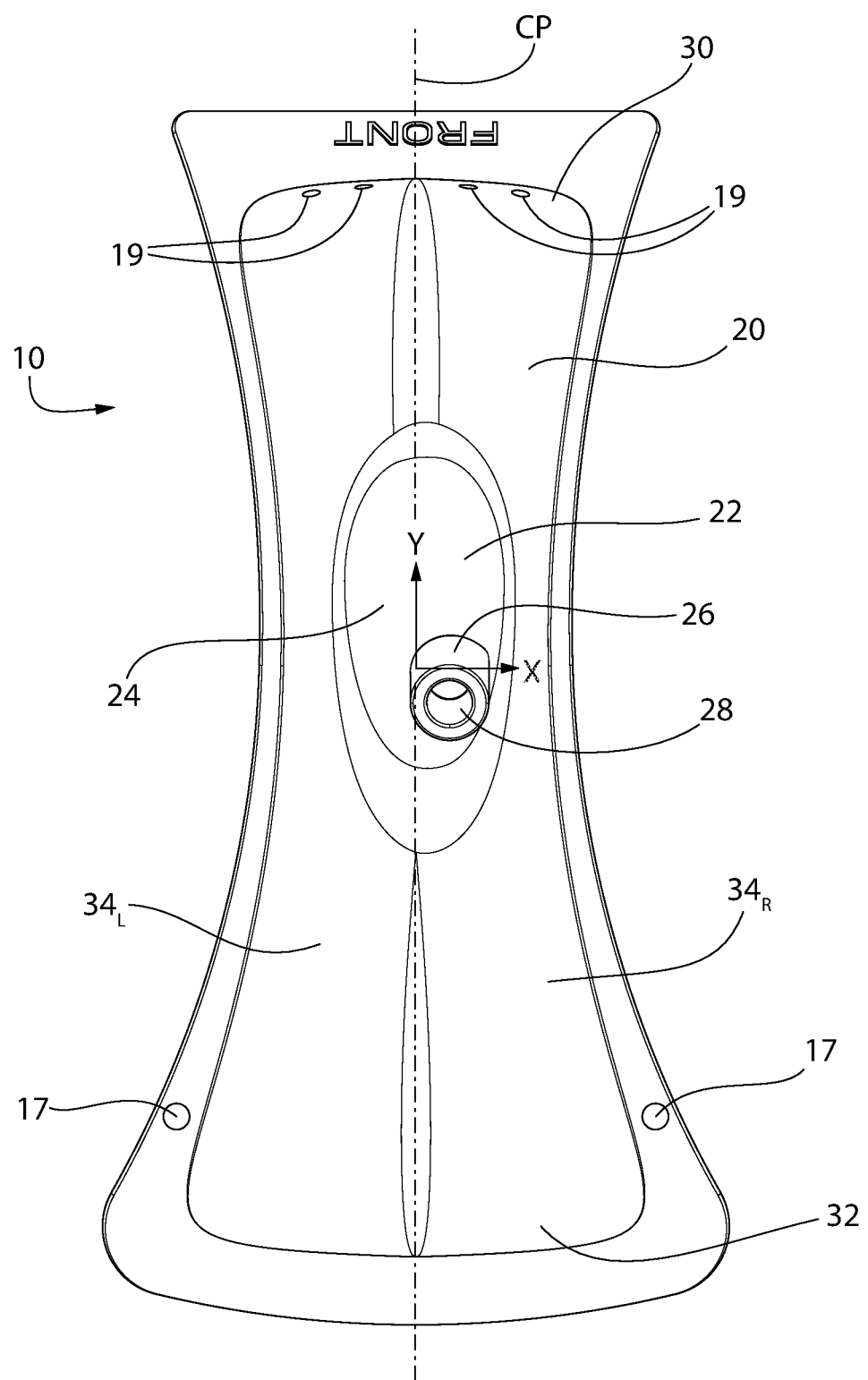
FIG. 8 is a bottom plan view of the device of FIG. 1.
Figure 9:
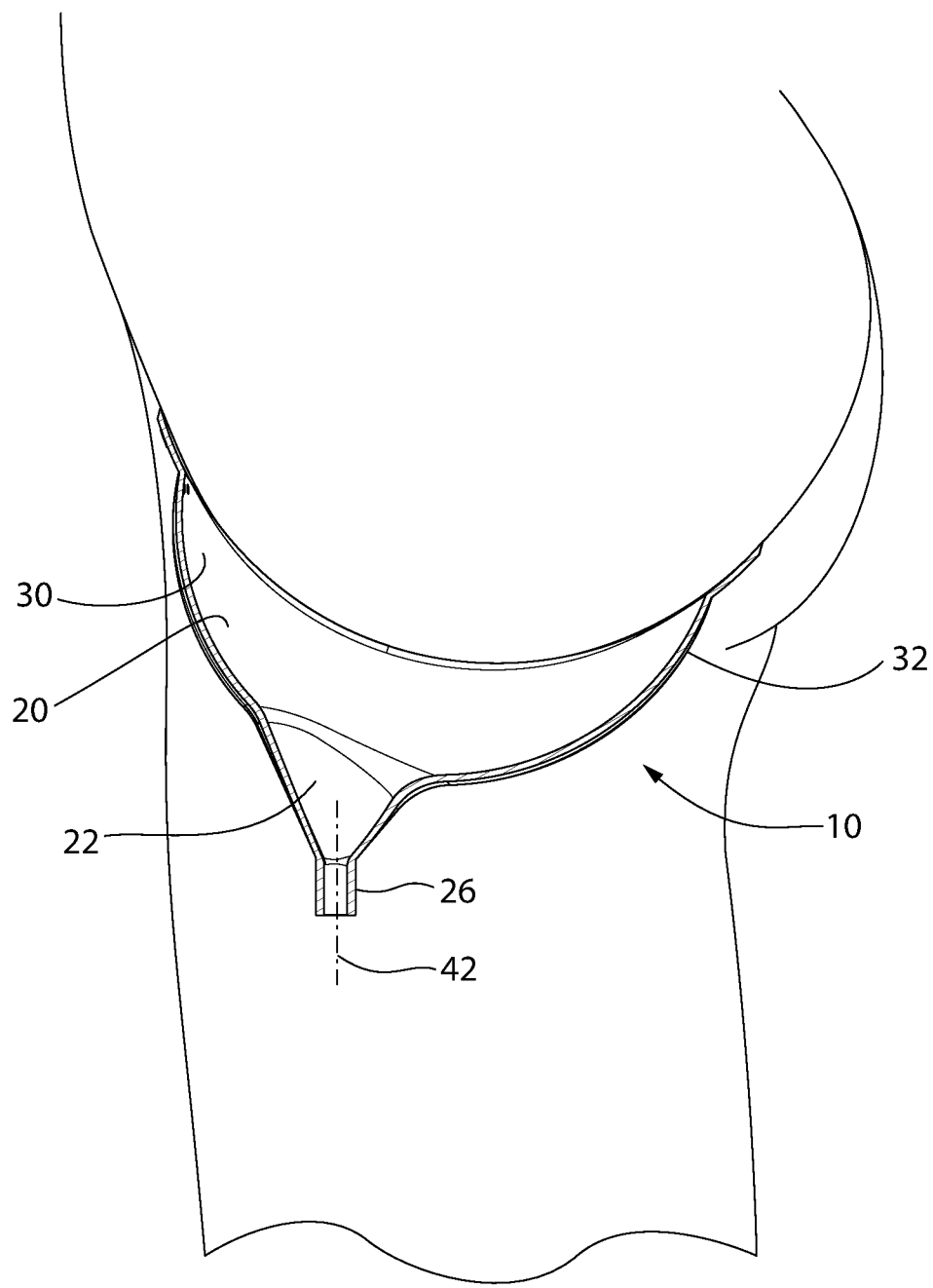
FIG. 9 is a section view along the sagittal plane of a wearer of the device of FIG. 1.

The tubular outlet 26 is optionally cylindrical and defines a central axis 42 (see, e.g., FIG. 6). The central axis 42 is preferably oriented at an angle θ relative to Z, angled downwardly and towards the rear of the device 10. The angle θ is preferably from 12° to 18°, more preferably from 14° to 16°, even more preferably from 14.5° to 15.5°. Optionally, the angle θ is 14° or about 14°, 15° or about 15°, 16° or about 16° or 17° or about 17°. The angled orientation of the funnel portion 22, including the outlet 26, towards the rear of the device 10, helps to facilitate moving excreted urine to the outlet opening 28. This angled orientation also helps to ensure that the outlet 26 is substantially vertical when worn properly. For example, as seen in FIG. 9, the central axis 42 of the outlet 26 is substantially vertical (i.e., substantially perpendicular to the flat ground) when the device 10 is worn. This configuration facilitates proper draining of the excreted urine. Without the angle, any flexible tube (discussed below) connected to the outlet opening 28 would point forward and likely be forced to bend or kink under the user's clothes, potentially causing the device to backup and overflow. Having this angled orientation also helps to keep the outlet 26 better aligned with the wearer's legs so that the device 10 can be worn comfortably and more securely under clothing. It also compensates for the forward tilt that would otherwise occur (without the described angled orientation). As such, the angled orientation prevents the outlet 26 from protruding forward, which could otherwise cause the wearer discomfort or be visibly noticeable from the outside when worn.

A vertically oriented central plane (CP) of the device 10 intersects the front section 30 and the rear section 32 of the device 10 and is coplanar with the YZ plane of the Cartesian coordinate system 40. Preferably, the upper ridge 14 and at least a substantial part of the collection portion 20 is symmetrical about the central plane CP. In any event, when the device 10 is worn as intended, the central plane CP is coplanar with the wearer's sagittal plane. As best seen in FIGS. 3 and 4, the central axis 42 of the outlet 26 is laterally offset by a distance D from the central plane CP. The distance D is greater than zero inches and is optionally from 0.1 to 0.5 inches, optionally about 0.25 inches. Preferably, the central axis 42 of the outlet 26 is parallel to the central plane CP. In the embodiment shown, the central axis 42 of the outlet 26 is offset to the left of the wearer's sagittal plane from the perspective of the wearer (i.e., it is closer to her left thigh than to her right thigh). But, the central axis 42 of the outlet 26 may alternatively be offset to the right of the wearer's sagittal plane from her perspective (i.e., closer to her right thigh than to her left thigh). This preferably slight offset to the right or left renders the outlet 26 asymmetrical with respect to the central plane CP or to the wearer's sagittal plane when worn. In this way, the outlet 26 is more aligned with the left or right leg and thus fits more easily on one side of the crotch, when pants or shorts are worn. This positioning also reduces the possibility that a flexible tube connected to the outlet 26 will kink.

Optionally, in any embodiment, the device 10 is made, preferably in its entirety, from medical grade silicone. Optionally, in any embodiment, the device 10 has a Shore A hardness of from 40 to 80, optionally from 60 to 80, preferably 70. The silicone having a durometer within the aforementioned ranges provides a comfortable fit and structural integrity to be used for the intended purpose. The medical grade silicone is approved for long-term skin contact and the durometer is flexible enough to wear comfortably but firm enough to substantially retain its shape under clothes. Further, silicone, as a hydrophobic material, facilitates the free flow and evacuation of urine from the device 10. The hydrophobic nature of silicone also prevents the material from absorbing the urine, allowing the device 10 to be readily cleaned and reused.

Optionally, in any embodiment, the funnel portion 22 is longer than the collection portion 20 is high. Optionally, in any embodiment, the funnel portion 22 is approximately the same height as the collection portion 20. Optionally, in any embodiment, the height of the funnel portion 22 is from 90% to 110% the height of the collection portion 20.

Optionally, in any embodiment, the device has a nominal wall thickness of 0.05 inches to 0.25 inches, optionally 0.07 inches to 0.18 inches, optionally 0.07 inches to 0.11 inches, preferably about 0.09 inches.

Optionally, in any embodiment, the housing wall 18 of the tubular outlet 26 adjacent the outlet opening 28 has a wall thickness that is approximately twice as thick as the wall thickness of the remainder of the housing wall 18. This thicker section of housing wall 18 at and near the outlet opening 28 is configured to prevent tears (and thus, leaks) where a reverse barb fitting may be secured to the outlet 26 when connecting a flexible tube thereto. Preferably, the inner diameter of the outlet 26 adjacent the outlet opening 28 is capable of accommodating the size and geometry of reverse barb connectors for flexible tubes and compatible urine bags on the market. Optionally, the inner diameter of the outlet opening 28 is from 0.25 to 0.5 inches, optionally from 0.3 to 0.4 inches, optionally about 0.33 inches, optionally 0.328 inches.

Figure 5:
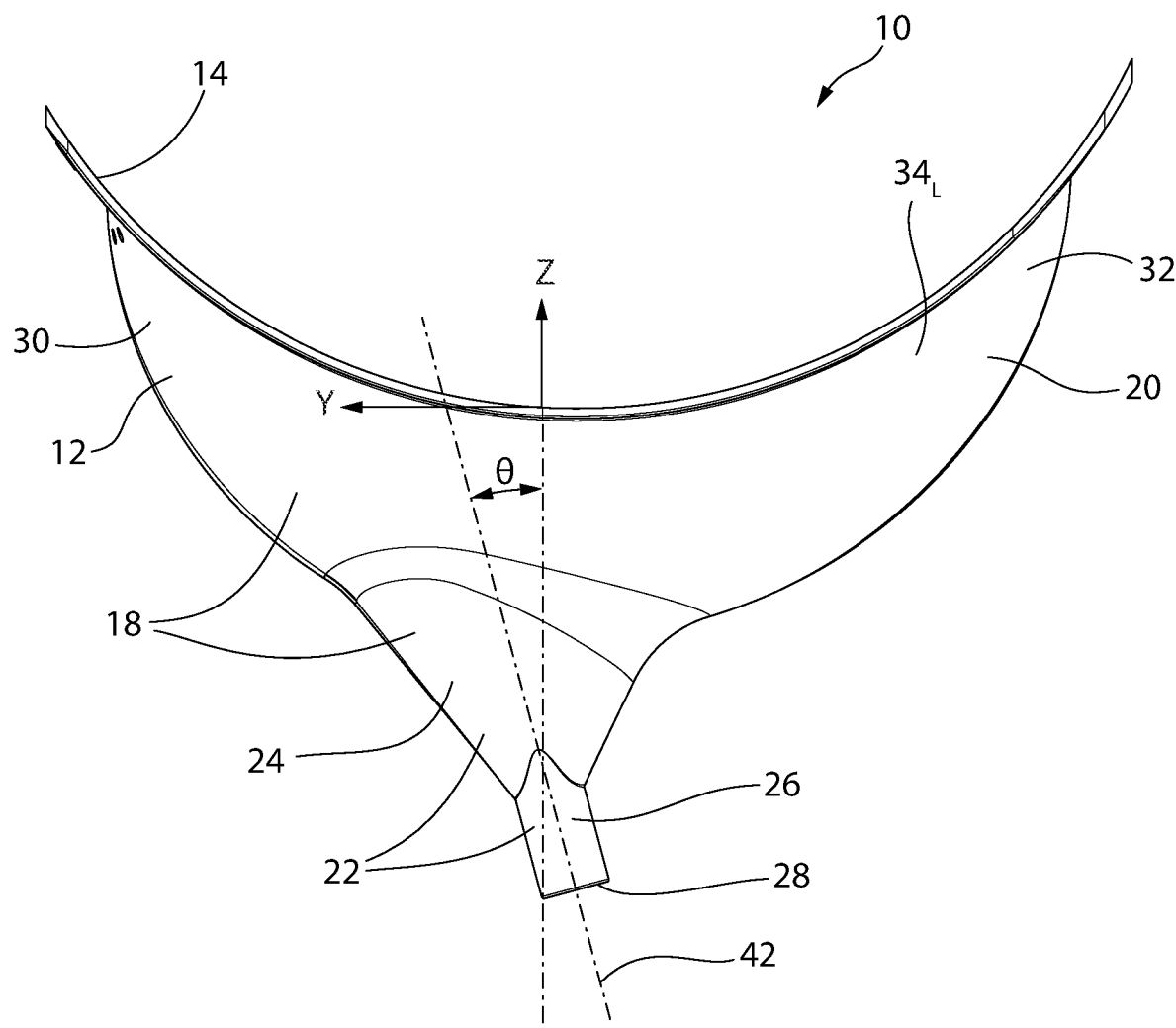
FIG. 5 is a left side elevation view of the device of FIG. 1.

Unless stated otherwise in a given instance, dimensional measurements of the device 10 are measured with the opposite ends of the flange 15 (extending from the front section 30 and rear section 32, respectfully) being of equal height, e.g., substantially as shown in FIG. 5. Thus, for example, the total length of the device 10 is measured, when in the aforementioned orientation, from the uppermost tip of the flange 15 of the front section 30 to the uppermost tip of the flange 15 of the rear section 32. The total height of the device is measured, when in the aforementioned orientation, from the uppermost tip of the flange 15 of the front section 30 vertically down to (i.e., perpendicular to) the horizontal plane that intersects the lowermost tip of the outlet 26. Optionally, in any embodiment, the total length of the device 10 is 8 to 9 inches, optionally 8.5 to 9 inches, preferably about 8.75 inches, and the total height is 6 to 7 inches, preferably about 6.5 inches. Optionally, in any embodiment, the crescent shape of the upper ridge 14 (from a side view, e.g., as shown in FIG. 5) is from 2.25 to 2.75 inches, preferably about 2.5 inches, when measured vertically from the horizontal plane tangent to the crescent-shaped curve at the lowest point on the upper ridge 14 (at the midpoint of the collection portion 20, lengthwise) to the uppermost point of the flange 15 of the front section 30 or rear section 32. Optionally, in any embodiment, the collection portion 20 has a depth, when measured vertically from the horizontal plane tangent to the crescent-shaped curve at the lowest point on the upper ridge 14 (at the midpoint of the collection portion 20, lengthwise) to the opening of the funnel portion 22 of 1.25 to 2.5 inches, preferably 1.75 inches.

Figure 10:
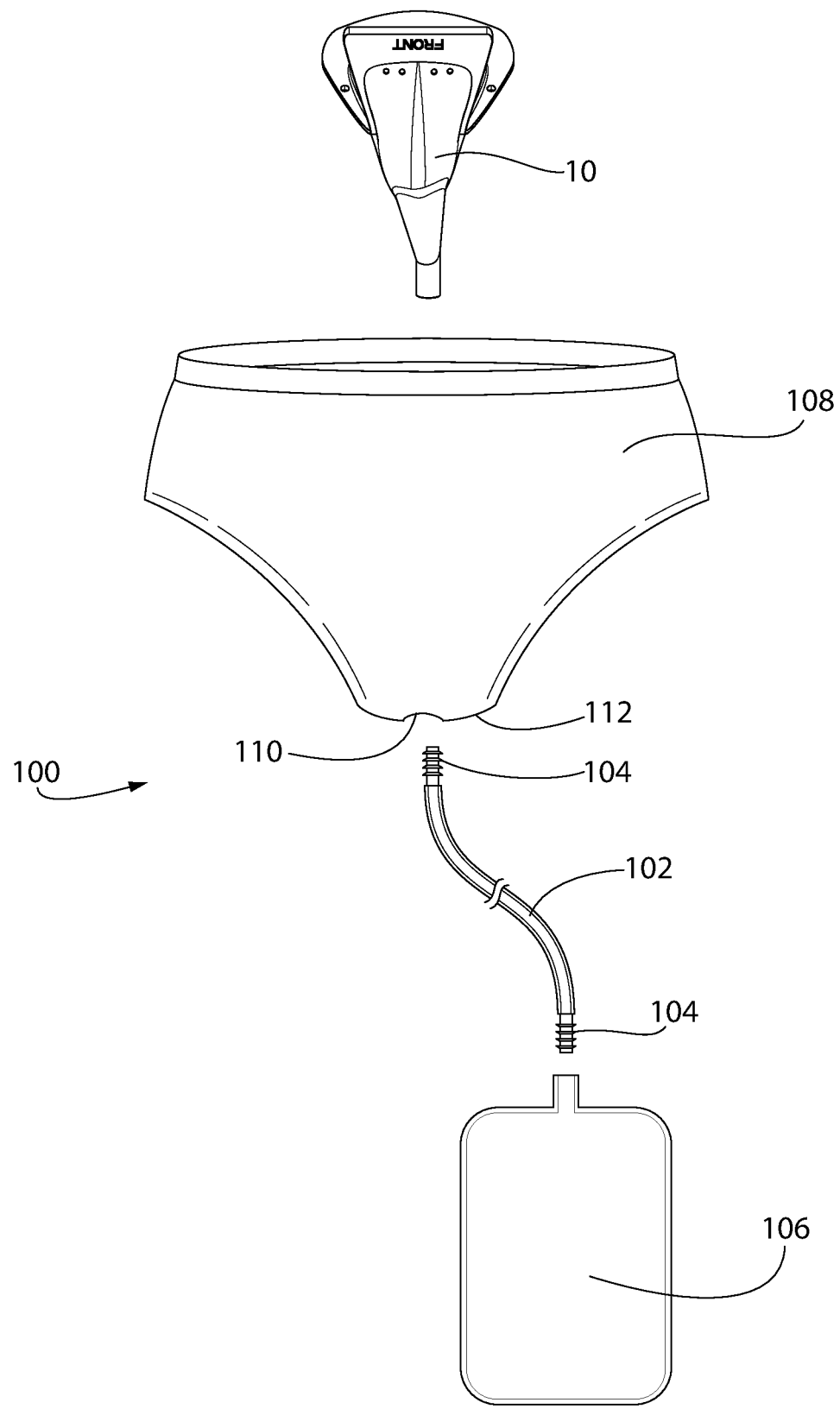
FIG. 10 is a view of components of a kit according to an optional aspect of the disclosed concept.
Figure 12:
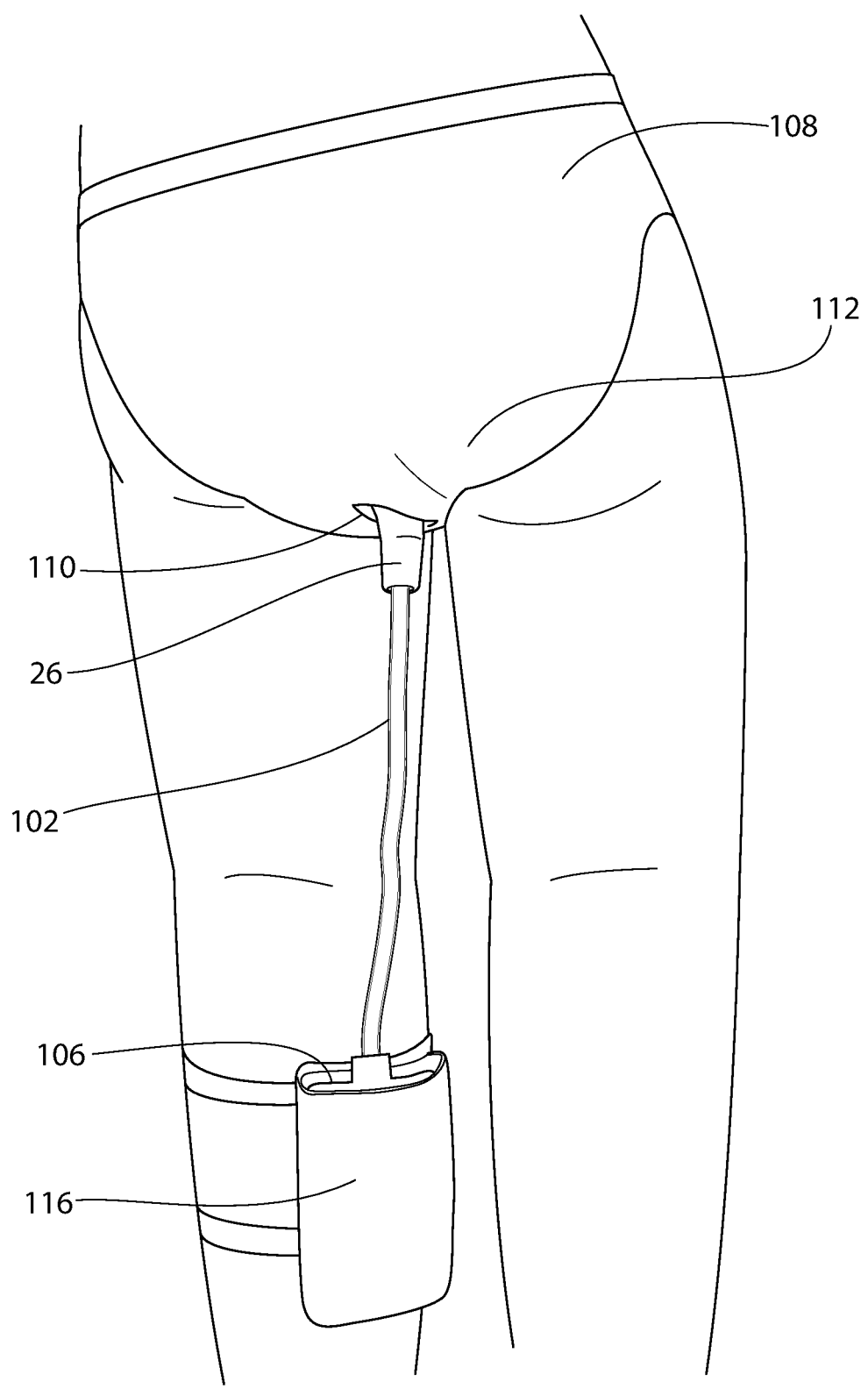
FIG. 12 is a partial isomeric view of a woman wearing the assembly or system of FIG. 11.

Optionally, as shown in FIG. 10, the device 10 is provided as a component of a kit 100. The kit 100 may comprise any of the following: (1) the device 10, (2) a flexible tube 102, (3) one or more connectors 104 and (4) a urine collection container 106, preferably a flexible urine bag. The connector 104 is preferably a reverse barb connector, which is a fitting used to sealingly connect tubular components to facilitate liquid tight fluid flow between the components. The connector 104 is configured to provide a robust liquid tight connection between one end of the flexible tube 102 and the outlet opening 28 to facilitate draining of urine from the device 10 into the flexible tube 102 when the device 10 is in use. A connector 104 may also be used to provide a liquid tight fluid connection between another end of the flexible tube 102 and the mouth of the urine collection container 106. The urine collection container 106 may optionally be retained to the body of the wearer, e.g., one of the wearer's legs. Optionally, as shown in FIG. 12, the urine collection container 106 is retained to the leg using straps or a wearable pocket 116 having a portion that enwraps a leg so as to be secured thereto. The straps or wearable pocket 116 may be an optional additional component of the kit 100. Optionally, the kit 100 includes one or more plugs that may be inserted into the outlet opening 28 to close and seal the opening when the connector 104 and flexible tube 102 are not being used. Each plug is optionally made from silicone and is configured to provide a liquid tight seal with the outlet opening to prevent drips and minor leaks from the device 100. Optionally, each plug includes a reverse barb connector configuration for inserting into the outlet opening 28 and a gripping portion that protrudes from the outlet opening 28 to enable a user to readily insert and remove the plug.

Figure 11:
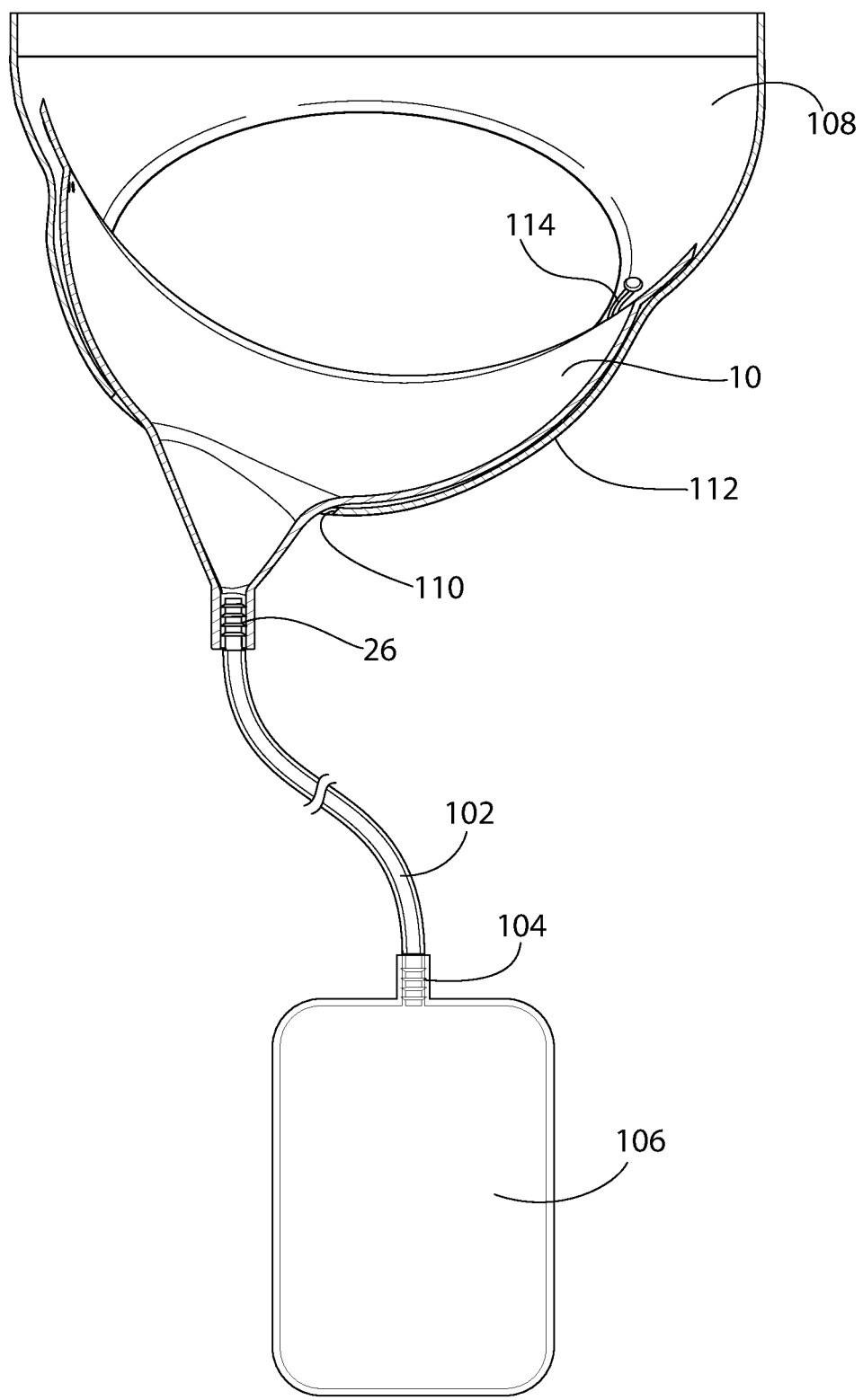
FIG. 11 shows an assembly or system of the components of the kit of FIG. 10.

Optionally, the kit also comprises at least one pair of underpants 108. The underpants 108 are configured to retain the device 10 over the wearer's crotch. As shown in FIGS. 10 to 12, the underpants 108 have an opening 110 in a bottom portion 112 (i.e., crotch area) thereof, through which the outlet 26 of the device 10 may protrude, where it can be connected to the flexible tube 102. The opening 110 is a feature distinct from the leg openings. The opening 110 is one feature that helps to retain the device 10 in its proper place when worn. The underpants 108 are preferably made from a stretch fabric that is machine washable. And, they might integrate some extra absorbent fabric surrounding the crotch area to protect against leaks. Alternatively, the underpants 108 may be disposable, with the opening 110 precut in production or created after purchase, e.g., by the wearer herself. The underpants 108 would optionally incorporate extra fabric in the bottom portion 112 to compensate for the height of the collection portion 20, essentially cradling the device 10 to help retain it in its intended place on the wearer. As an optional further feature to ensure proper placement and positioning of the device 10 on the wearer, a plurality of fastener components 114 may be provided to retain the device 10 to the underpants 108. Exemplary fastener components 114 may include snaps, hook and loop fasteners, buttons, ties and the like. The fastener components 114 may secure the underpants 108 to the holes or slits 17 in the flange 15 of the device 10 to help keep the device 10 in its proper position when worn.

In addition, or alternatively, special linings, special openings, or special pockets could be integrated into companion undershorts, legging undergarments and other outer garments as well. Similar to the underpants 108, other companion undergarments would have an opening in the crotch area, through which the outlet 26 of the device 10 may protrude. And special linings, special openings, or special pockets in those garments could provide added benefits for the user. For example, a pocket on the inner-thigh area of companion undershorts could encase the outlet 26, to reduce the chance that the device 10 will be visible to others when the user is wearing a short skirt over top. And the pocket could also add comfort for the user, as soft cloth material could prevent the outlet 26 from rubbing directly on the user's thigh. The inside of the pocket may also include a waterproof material that would prevent urine from leaking on the user's leg after use, when the device 10 is being worn without a connection to a urine collection container 106.

Optionally, pants designed for outerwear could integrate a special zipper opening in the inner-thigh area. This could enable the user to access the outlet opening 28 and therefore use the device 10 to excrete urine through the outlet opening 28 to a location outside of her pants (e.g., into a hand-held collection container, a toilet, an outhouse, the ground, etc.) when she is not wearing a urine collection container 106. Optionally, a special lining in companion legging undergarments could make it possible to encase the flexible tube 102 to keep the tube 102 snug to the leg, thereby reducing visibility and also reducing risk of kinks or disconnection from the wearer's movements. The lining could optionally lead to a special pocket integrated within the legging undergarment that is configured to hold the urine collection container 106. A special lining that encases the flexible tube 102 could optionally lead to a special pocket that is accessible from the user's outer garments, as well, for occasions like skiing where it might be preferable to access a urine collection container 106 from the outer pant. The special pockets designed to hold urine collection containers 106 optionally include openings along the bottom seams to accommodate drainage valves.

Optionally, companion legging undergarments might pair with outer pants that both detach above the knee (e.g., like convertible pants-to-shorts). The bottom portion of the legging may be designed to hold the urine collection container 106 in a special pocket, snug to the leg, while an outer pant material hides any bulges that the container 106 or the device 10 may create. A user wearing these custom convertible pants-to-shorts on a hike, for example, could detach the bottom portion of the outer pants and leggings, along with the collection container 106 and flexible tube 102, while continuing to wear the top portion of the outer pants and leggings, leaving the device 10 underneath, intact. Even without a urine collection container 106, the user may use the device 10 without disrobing by holding up a container to the outlet opening 28 when she is ready to expel urine. Other outerwear, such as jogging shorts or skirts, could be created to pair with companion undergarments, like undershorts, or be designed to integrate the companion undergarment. Optionally, any outerwear that is integrated with or paired with companion undergarments could be designed with extra room in the crotch area, or added pant width, to accommodate for the added bulk that results from wearing the device 10 or any kit components.

The features and structure of the device 10 render it particularly suitable as an externally wearable female urinary collection and drainage device that may be used without disrobing while standing, for example. The Applicant has found that the combination of two or more of the following optional features and structure render the device 10 unique over and advantageous compared to prior art devices. Such features and structure include the following:

- The collection portion 20 is substantially sized to provide a holding area for urine that does not drain immediately. The collection portion 20 and funnel portion 22 should be deep or high enough to prevent overflow of urine while not too deep such that it is difficult to conceal or uncomfortable to wear.
- The funnel portion 22 is thinner than the collection portion 20 so that it is less likely to show in the wearer's clothes and is less likely to interact with the thighs, e.g., when the wearer is walking or running.
- The device 10 is made of a flexible, medical grade silicone that maintains its shape while still being comfortable to wear.
- The collection portion 20 covers the entire span of the mons pubis to the perineal region. It has a crescent shape from a side view and concave sides from a top view that conforms to the female crotch area. These aspects help to provide leak protection and to hold the device 10 in place comfortably.
- The funnel portion 22 is located forward of center, so as to align with the urethra, helping urine to exit more quickly and prevent pooling of urine. And, having a funnel portion 22 that is about as long as the collection portion 20 is deep enables the funnel portion 22 to act as a second collection area.
- The size of the funnel portion 22 together with its angle towards the rear of the device 10 helps to keep the urine flow approximately perpendicular to the ground so it drains properly. And the angle also helps keep the funnel portion 22 hidden under clothes.
- Vent holes 19 help to prevent air from pressurizing the device 10, the flexible tube 102 and/or the urine collection container 106 which might be caused by movement of the wearer's legs.
- The flange 15 improves comfort and provides an area for holes or slits 17 that can be used with fastener components 114 so users can attach the device 10 to underpants 108, helping to keep the device 10 in its proper position when worn.
- The optional slight offset of the outlet 26 to the right or left helps to keep it aligned with the thigh, reducing the likelihood that any connected tube might kink if worn under pants and helping to conceal it under clothes more easily.
- The outlet opening 28 is sized to enable a connection to urine bags via reverse barb connectors with tubing.

The aforementioned features, optionally, but preferably in combination, offer significant improvement over prior art devices that are designed to require disrobing before use (e.g., at a urinal or the like). Also, an external device, such as described herein, which is ready to wear, washable, and re-usable, that needs (if desired) only slightly modified underwear to stay in place, provides a much-needed, cost-saving alternative to the disposable absorbent products on the market for active women who suffer from Overactive Bladder or other incontinence issues.

While the invention has been described in detail and with reference to specific examples thereof, it will be apparent to one skilled in the art that various changes and modifications can be made therein without departing from the spirit and scope thereof.

What is claimed is:

1. A urinary collection and drainage device configured to be externally worn on a crotch region of a female wearer and used while the wearer is upright and her legs and torso are oriented generally vertically, the device comprising a housing having an upper ridge configured to contact the wearer's crotch and surround her vagina, the upper ridge having a crescent-shaped rise from a side view, the upper ridge surrounding an upper opening of the device and having an outwardly projecting flange, the device comprising a housing wall extending from the upper ridge, the housing wall defining a collection portion and a funnel portion extending from the collection portion, the collection portion being configured to substantially cover the vagina so as to receive, temporarily hold and facilitate directional flow of urine that the wearer excretes into the funnel portion, the funnel portion being defined by an inwardly tapered section of the housing wall and a tubular outlet to which the inwardly tapered section leads, the outlet comprising an outlet opening, the collection portion having a front section comprising a front portion of the flange that constitutes part of the rise and which is configured to contact the wearer's mons pubis, a rear section comprising a rear portion of the flange that constitutes part of the rise and which is configured to contact the wearer's perineal region and opposing side sections linking the front section and rear section, the side sections being concave in shape from a top view, the rise from the side view having a vertical measurement from a horizontal plane tangent to a curve at a lowest point on the upper ridge to a horizontal plane intersecting both an uppermost point of the front portion of the flange and an upper most point of the rear portion of the flange, the collection portion from the side view having a depth measured vertically from the horizontal plane tangent to the curve at the lowest point on the upper ridge to a transition section in which the collection portion transitions to the funnel portion, the funnel portion having an outer width that is narrower than an outer width of the collection portion and a funnel height which from the side view has a vertical measurement from the transition section to a lowermost tip of the outlet, wherein a front of the inwardly tapered section has a front length and a rear of the inwardly tapered section has a rear length, the front length being of a dimension at least equal to the depth of the collection portion so that when the device is worn by the wearer with the front portion of the flange contacting the wearer's mons pubis and the rear portion of the flange contacting the wearer's perineal region, the outlet would be positioned substantially below the wearer's urethra, the outlet defining a central axis that is oriented at an angle inclined downwardly and towards the rear of the device from about 14° to 17° relative to a vertical axis (Z) of a three-dimensional Cartesian coordinate system, wherein the central axis is located at a horizontal distance substantially closer to the front section than to the rear section to position the transition section substantially below the wearer's urethra, wherein the angle configures the central axis to be oriented substantially perpendicular to a surface on which the wearer stands when the front portion of the flange contacts the wearer's mons pubis and the rear portion of the flange contacts the wearer's perineal region, thereby facilitating moving excreted urine downward to the outlet opening and substantially aligning the outlet with the wearer's vertically oriented legs, the device defining an imaginary vertically oriented central plane that intersects the front section and the rear section, wherein the upper ridge and at least part of the collection portion is symmetrical about the central plane, the central axis of the outlet being offset by a distance greater than zero inches from the central plane to render the funnel portion closer to and more aligned with one leg than the other.

2. The device of claim 1, wherein the vertical measurement of the rise is 2.25 to 2.75 inches.

3. The device of claim 1, wherein the collection portion depth measured vertically is from 1.25 to 2.5 inches.

4. The device of claim 1, wherein from the side view, a front view and a rear view, the inwardly tapered section of the housing wall defining the funnel portion has a steeper slope than the portion of the housing wall defining the collection portion.

5. The device of claim 1 comprising one or more vent holes positioned on the front section, adjacent the upper ridge.

6. The device of claim 1, wherein the device is made from medical grade silicone having a durometer of from 60 to 80.

7. The device of claim 6, wherein the device has a nominal wall thickness of 0.07 inches to 0.11 inches.

8. The device of claim 1, wherein from a top view, the rear section has a width greater than that of the front section, the rear section has a total width of about 5 inches and the front section has a total width of about 4 inches, the device having concave side sections that taper inwardly to a width of from 2 to 3 inches at a narrow middle section.

9. The device of claim 1, wherein the device is made of a flexible material and is configured to retain its shape when worn under clothes.

10. The device of claim 1, wherein the inner diameter of the outlet opening is about 0.328 inches.

11. The device of claim 1, having a total length of about 8.5 to 9 inches.

12. The device of claim 1, in which the total length of the device is greater than a total height of the device.

13. The device of claim 1, wherein the funnel height is at least 75% of the collection portion depth measured vertically.

14. A kit comprising at least one member of each of: (i) the device of claim 1; (ii) at least one pair of underpants having an opening in a bottom portion thereof, in addition to leg holes, though which the outlet of the device may protrude; (iii) a flexible tube; (iv) a connector; and (v) a urine collection container that is configured to be strapped to a wearer's leg or secured to the wearer's clothing;
  wherein one end of the flexible tube can be secured to the outlet opening via the connector so as to establish a liquid tight fluid connection between the device and the flexible tube, wherein the other end of the flexible tube can be secured, in a liquid tight fluid connection, to a mouth of the urine collection container so as to enable liquid to flow through the flexible tube and into the urine collection container.

15. A method for a female wearer to sanitarily urinate with her clothes on when she is upright and her legs and torso are oriented generally vertically and without use of an internal catheter or padding to absorb excreted urine, the method comprising:
  a. placing the device of claim 1 on the crotch region of the wearer such that the upper ridge contacts the wearer's crotch and surrounds her vagina, the front portion of the flange contacts the wearer's mons pubis and the rear portion of the flange contacts the wearer's perineal region so as to orient the central axis of the outlet substantially perpendicular to a surface on which the wearer stands;
  b. wearing a pair of underpants over the device, the underpants having a bottom portion that cradles the device so as to retain the device on the wearer's crotch region, the underpants having an opening in the bottom portion in addition to leg holes, the outlet of the device protruding through the opening in the bottom portion of the underpants; and
  c. urinating into the device such that excreted urine exits the device through the outlet opening.

16. The method of claim 15, the method further comprising, prior to step (c), securing a first fluid connection between the outlet opening and a first end of a flexible tube, securing a second fluid connection between a second end of the flexible tube and a mouth of a urine collection container and securing the urine collection container to an appendage of the wearer or onto clothing of the wearer;
  wherein after step (c), excreted urine flows from the device, through the flexible tube and into the urine collection container.

17. The method of claim 16, wherein air supplied into the device from movement of the wearer's legs, escapes through the one or more vent holes to prevent the air from pressurizing the device, the flexible tube and/or the urine collection container.

18. The method of claim 15, wherein the device is oriented to have a substantially steeper slope from the front section to the outlet than from the rear section to the outlet.

19. The device of claim 1, wherein the front portion of the flange and rear portion of the flange are each from about 0.5 to 1 inch wide.

20. The device of claim 1, wherein the front length of the inwardly tapered section is 2 to 2.75 inches, the rear length of the inwardly tapered section is 1 to 1.75 inches and the tubular outlet is 0.5 to 1 inch in length.

21. The device of claim 1 having a total height of 6 to 7 inches, measured vertically from the lowermost tip of the outlet to the horizontal plane intersecting both the uppermost point of the front portion of the flange and the uppermost point of the rear portion of the flange.

22. The device of claim 1, wherein the transition section defines a transition opening leading from the collection portion to the funnel portion, the transition opening being about 1.5 to 2.5 inches long and about 0.5 to 1.5 inches wide, the transition opening being located to the front of center of the collection portion.

\* \* \* \* \*